(12) United States Patent
Winkler et al.

(10) Patent No.: US 8,931,357 B2
(45) Date of Patent: Jan. 13, 2015

(54) COAXIAL NEEDLE AND PIPETTING DEVICE

(75) Inventors: Siegfried Winkler, Heidelberg (DE); Christian Conrad, Edingen (DE)

(73) Assignee: EMBL European Molecular Biology Laboratory, Heidelberg (DE)

( * ) Notice: Subject to any disclaimer, the term of this patent is extended or adjusted under 35 U.S.C. 154(b) by 0 days.

(21) Appl. No.: 13/132,711

(22) PCT Filed: Dec. 3, 2009

(86) PCT No.: PCT/EP2009/008637
§ 371 (c)(1),
(2), (4) Date: Jun. 24, 2011

(87) PCT Pub. No.: WO2010/063474
PCT Pub. Date: Jun. 10, 2010

(65) Prior Publication Data
US 2011/0277565 A1 Nov. 17, 2011

(30) Foreign Application Priority Data

Dec. 4, 2008 (EP) ..................... 08170677

(51) Int. Cl.
*G01N 35/10* (2006.01)
*B01L 3/02* (2006.01)
(52) U.S. Cl.
CPC .............. *B01L 3/02* (2013.01); *G01N 35/1009* (2013.01); *B01L 2300/0832* (2013.01); *B01L 2300/0854* (2013.01); *B01L 2400/0487* (2013.01); *B01L 2400/049* (2013.01)
USPC ..................................................... 73/864.25
(58) Field of Classification Search
None
See application file for complete search history.

(56) References Cited

U.S. PATENT DOCUMENTS

| | | | | |
|---|---|---|---|---|
| 3,960,020 A | | 6/1976 | Gordon et al. | |
| 4,713,974 A | * | 12/1987 | Stone | 73/864.23 |
| 4,933,148 A | * | 6/1990 | Perlman | 422/513 |
| 5,015,591 A | * | 5/1991 | Meyrat et al. | 436/178 |
| 5,220,947 A | | 6/1993 | Cauquil et al. | |
| 5,569,861 A | * | 10/1996 | Le Comte et al. | 73/864.22 |

(Continued)

FOREIGN PATENT DOCUMENTS

| | | |
|---|---|---|
| GB | 895040 | 4/1962 |
| JP | 63-160943 | 10/1988 |

(Continued)

OTHER PUBLICATIONS

International Search Report dated Jun. 5, 2010.

(Continued)

*Primary Examiner* — Robert R Raevis
(74) *Attorney, Agent, or Firm* — RatnerPrestia

(57) ABSTRACT

A two-part coaxial needle for a pipetting device, in particular for use in microscopy of cell probes, makes it possible both to inject a liquid into a pipetting container and to remove by suction a liquid from the pipetting container. Both the drive for lowering the coaxial needle into the pipetting container, and injection and removal by suction of the liquid take place pneumatically by way of only one pressure source. The design of the coaxial needle and of the drive systems makes possible fast and reliable pipetting with high metering accuracy and a particularly compact pipetting unit which without mutual interference can be used with a multitude of widely-used microscope types.

13 Claims, 5 Drawing Sheets

(56) References Cited

U.S. PATENT DOCUMENTS

Figure 4A:
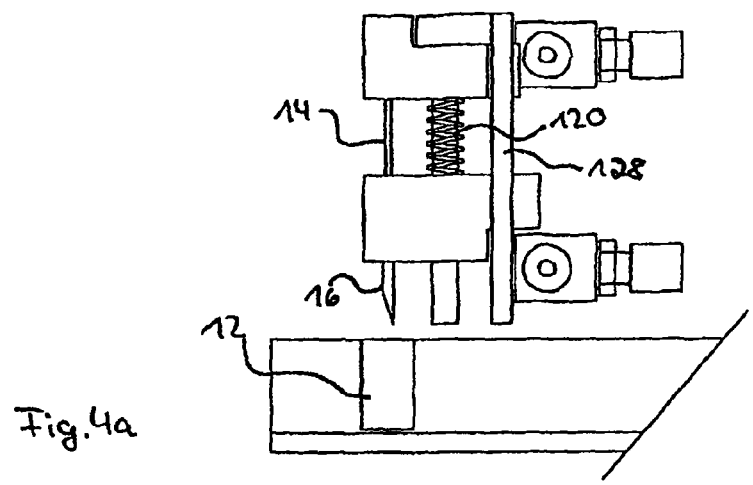

| | | |
|---|---|---|
| 6,938,502 B2 * | 9/2005 | Tanoshima et al. ........ 73/863.01 |
| 7,092,151 B2 | 8/2006 | Otaki et al. |
| 2002/0131902 A1 * | 9/2002 | Levy .............................. 422/99 |
| 2005/0012990 A1 | 1/2005 | Otaki et al. |
| 2005/0223822 A1 * | 10/2005 | Ozbal ........................ 73/864.41 |

FOREIGN PATENT DOCUMENTS

| | | |
|---|---|---|
| JP | 08-101206 | 4/1996 |
| WO | 9222798 | 12/1992 |

OTHER PUBLICATIONS

Written Opinion Dated Jun. 5, 2010.

* cited by examiner

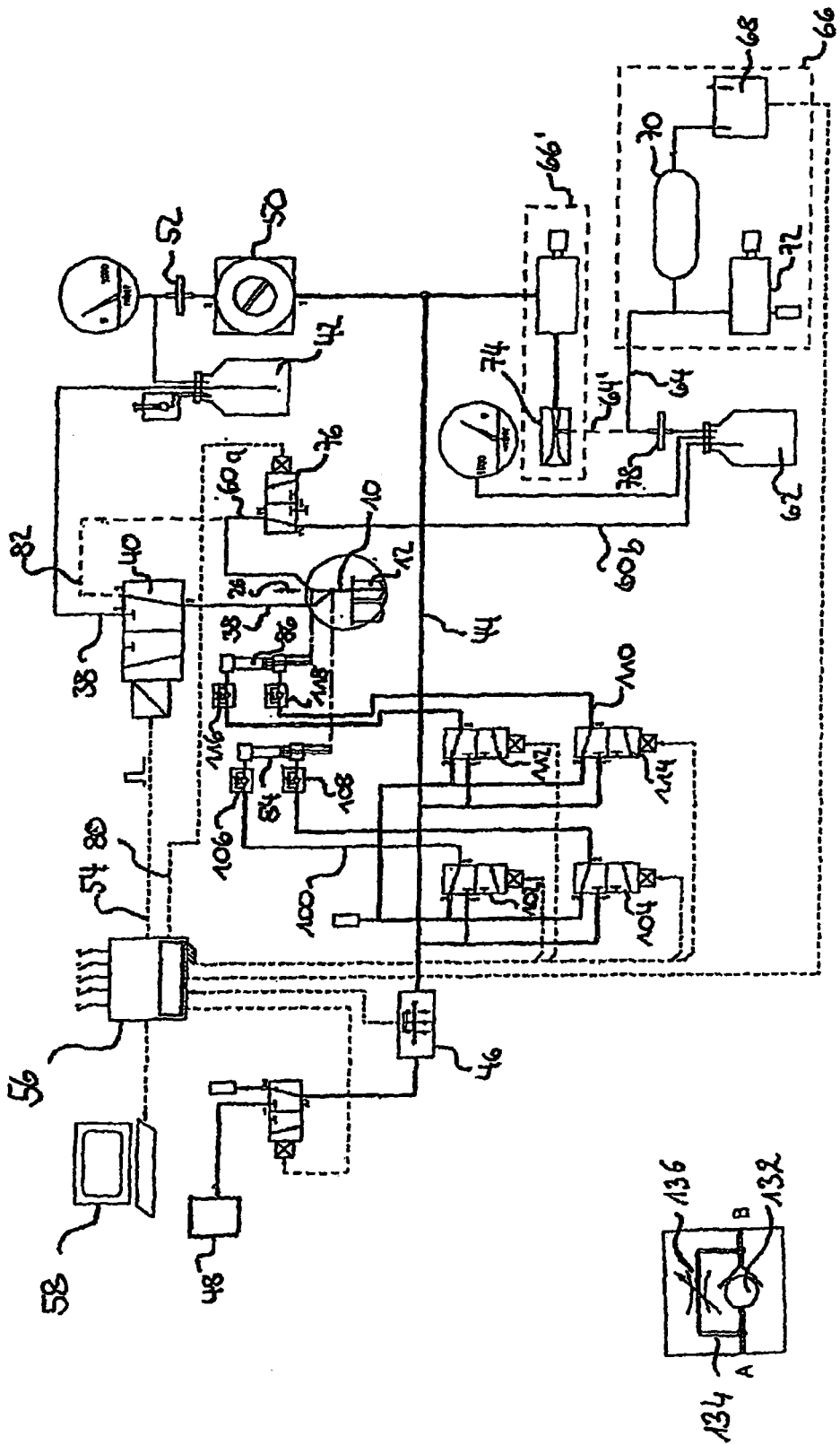

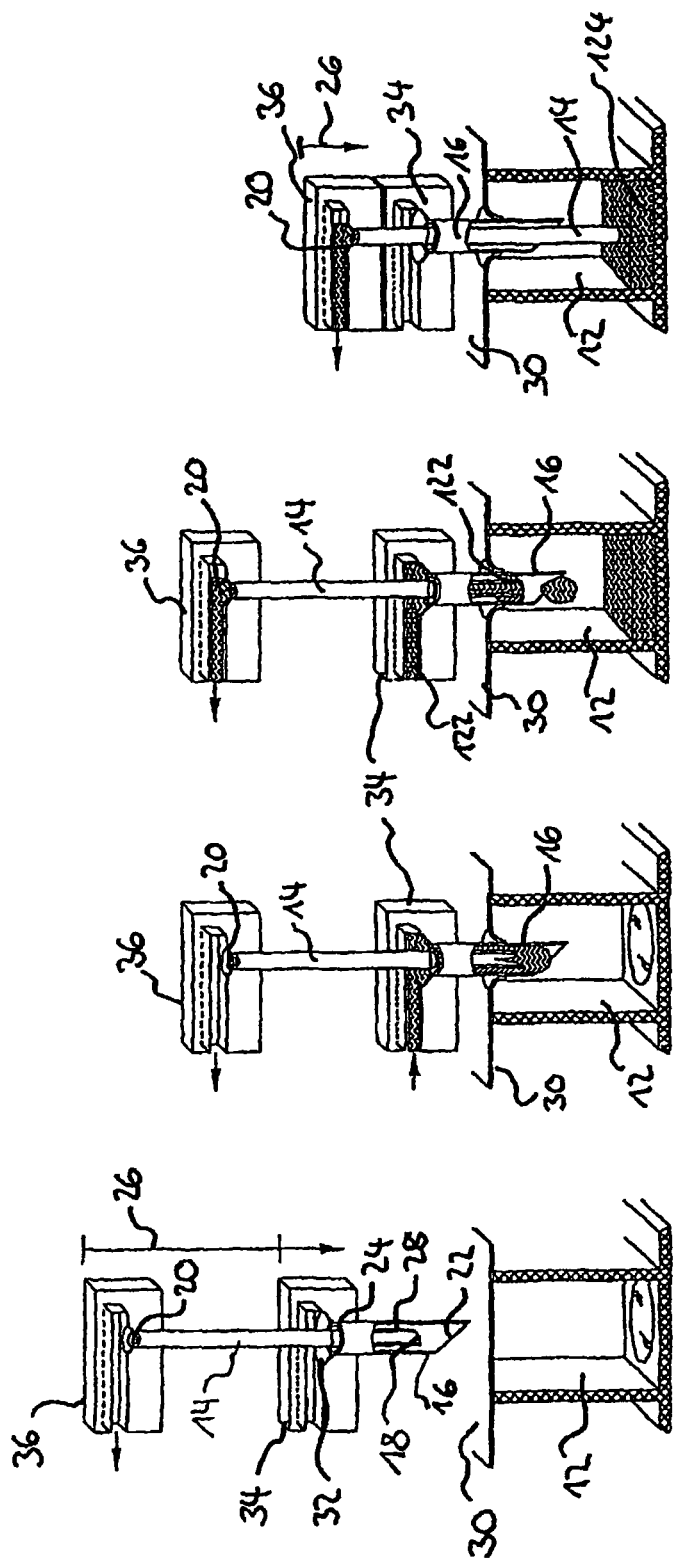

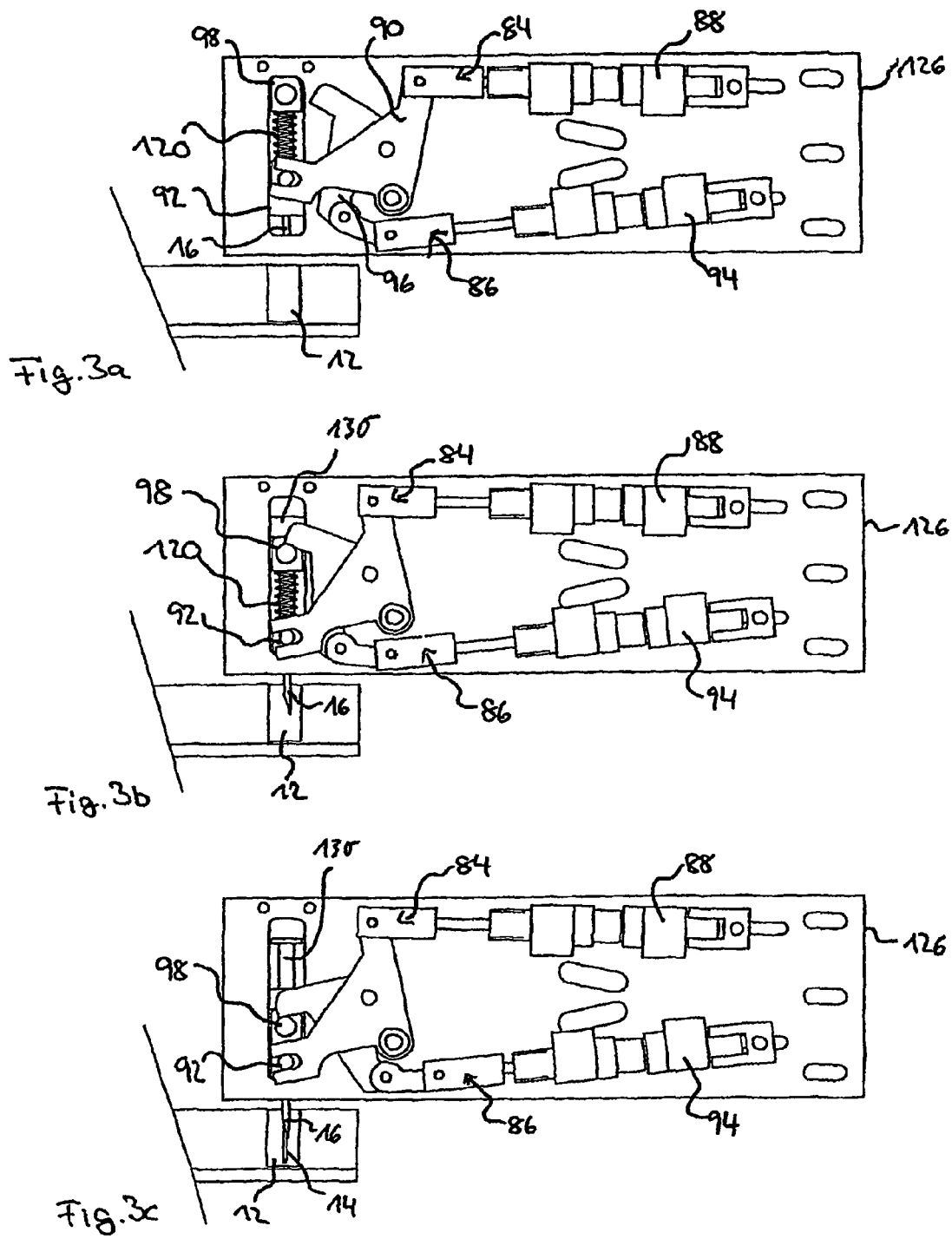

COAXIAL NEEDLE AND PIPETTING DEVICE

CROSS-REFERENCE TO RELATED APPLICATIONS

This patent application is a United States national phase patent application of International Patent Application No. PCT/EP2009/008637, filed Dec. 3, 2009, which claims priority to European Patent Application No. 08170677.2, filed Dec. 4, 2008, which applications are incorporated herein by reference in their entirety for all purposes.

FIELD OF THE INVENTION

The present invention relates to a pipetting device for use in microscopy, in particular in microscopy relating to cell probes.

BACKGROUND OF THE INVENTION

Test series with living cells are of paramount importance in biological and medical research and development, and are used to a large extent in the pharmaceutical industry, for example in the development of new active substances and medicaments. In this context there is a requirement for observing a multitude of different cell probes quickly and as far as possible in an automated manner by means of transmission microscopy or fluorescence microscopy, and during observation or between subsequent observation steps to feed, in a controlled manner, to the individual probes liquid substances which can, for example, comprise an active medical substance or some molecular-biological modification (e.g. siRNA or immunostaining).

To this purpose cell probes are distributed to separate chambers of an object carrier or of a multiwell plate, and for observation said probes, on a stage, are sequentially fed into the optical path of a microscope. In this process inverse microscopes are frequently used in which the image recording device and often also at least part of the illumination device are arranged below the stage so that the space above the stage can predominantly be reserved for positioning and filling the probe. For quick automatic positioning of the probes, generally speaking probe positioners are provided on the stage, which probe positioners can accommodate a multitude of different probe containers, wherein the individual probe chambers of said probe positioners can quickly and very accurately be moved into the optical path of the microscope, and for focussing can also be displaced along the optical axis. Adding a liquid, for example an active substance, at a determined dilution ratio or mixing ratio to the individual probe chambers, or removing the liquid by suction from the probe chambers, in part still takes place manually, for example with the use of a microliter pipette. However, manual filling or removal by suction is not only time-consuming and labour-intensive, but also quite error-prone.

Furthermore, it is often necessary to carry out test series under controlled temperature conditions and atmospheric conditions so that the probe container, together with the stage and parts of the observation equipment and illumination device, is accommodated in a so-called climatic chamber, and consequently the probes are practically no longer accessible from the exterior. For this reason automated pipetting systems with movable pipettes were invented, which systems make it possible to quickly and reliably feed a liquid into selected pipetting containers in a controlled atmosphere. In this arrangement, the liquid infeed from a reservoir normally takes place with the use of pumps comprising micro motors; positioning and operation of the pipette also takes place with the use of electric motors. An inverse microscope with such an automated pipetting device within a climatic chamber is, for example, described in patent specification U.S. Pat. No. 7,092,151 B2.

The pipetting devices known from prior art are associated with a difficulty in that the pipette and the drive unit require comparatively large installation space, and as a result of this they could negatively affect operation of the microscope. This problem occurs in particular if the probes in transmission are to be illuminated from above the stage, because the illumination device and the pipetting device cause mutual interference. However, the same difficulties can also arise in test series in which the illumination can be exclusively from below the stage, while the microscope used normally provides for a second illumination device above the stage, which second illumination device, while not needed for the test series that is to be carried out, nonetheless for design reasons cannot be moved out of the optical path far enough to allow unrestricted operation of the automatic pipetting device. Many widely used microscope types are associated with such spatial restrictions and can therefore be used with automatic pipetting devices known from prior art only with functional limitations or only after possibly time-consuming and cost-intensive modifications. There is thus a requirement for a pipetting device that can be used without mutual interference with microscopes of a known and widely used design.

Furthermore, the probe chambers used are often sealed by means of a cover, for example a metal foil or a plastic film, in order to protect the probe from the ambient atmosphere. There is thus furthermore a requirement for an automatic pipetting device which despite such a sealing arrangement makes it possible to quickly, reliably and precisely feed a liquid into selected probe chambers.

Likewise, apart from allowing automated feed-in of a liquid into selected probe chambers, the pipetting device should also allow the quick and effective removal of a liquid from selected probe chambers.

These objects are met by the coaxial needle according to the invention according to claim 1, or by the pipetting device according to the invention according to claim 5 and claim 11. The invention also relates to the corresponding pipetting method according to claim 13. The subordinate claims relate to preferred embodiments.

SUMMARY OF THE INVENTION

The coaxial needle according to the invention, for a pipetting device, comprises a hollow suction lance for drawing off a liquid from a pipetting container, as well as a hollow insertion lance that encloses the suction lance at least in part so that between an exterior wall of the suction lance and an interior wall of the insertion lance a liquids duct for feeding a liquid into a pipetting container is formed.

The liquids duct can, in particular, comprise the entire hollow space between the exterior wall of the suction lance and the interior wall of the insertion lance.

The coaxial needle according to the invention allows careful and precise metering of the quantity of liquid to be fed in, both with droplet injection and with injection in continuous flow.

In a preferred embodiment, the insertion lance coaxially encloses the suction lance. This makes it possible to achieve particularly even liquid feed-in.

In a further preferred embodiment the suction lance and/or the insertion lance are/is designed in the shape of a hollow cylinder or of a truncated hollow cone.

Furthermore, in a preferred embodiment the suction lance comprises a first open end for the uptake of a liquid from a pipetting container, and a second open end, which is arranged axially opposite the first open end, for the delivery of the taken-up liquid to a suction removal nozzle.

Furthermore, the insertion lance preferably comprises a first open end for the delivery of a liquid to a pipetting container, and a second open end, which is arranged axially opposite the first open end, for the uptake of a liquid from an insertion nozzle.

The liquid to be fed in can be fed to the liquids duct from the insertion nozzle by way of the second open end of the insertion lance, and can be fed into the pipetting container by way of the first open end of the insertion lance, which end is axially opposite the second open end. Likewise, a liquid from the pipetting container can be removed by suction through the first open end of the suction lance into the interior of the suction lance, from where it can be delivered to the suction removal nozzle by way of the second open end, which is situated axially opposite the first open end. By means of the coaxial needle according to the invention, liquids can quickly and in a metered manner be injected into the pipetting container, and they can also be removed from the pipetting container.

In a preferred embodiment, the first open end of the insertion lance comprises an insertion tip. In particular, the first open end of the insertion lance can be pointed so as to be bevelled. In this manner liquids can also be fed to pipette containers that are sealed by means of a cover, or they can be removed from such pipetting containers.

In a further preferred embodiment the first open end of the suction lance is arranged in the interior of the insertion lance. On the one hand, this provides an advantage in that the suction lance is effectively protected from damage when puncturing sealed pipetting containers. On the other hand, an arrangement of the suction lance in the interior of the insertion lance has an advantageous effect on liquid metering. The liquid entering the liquids duct flows around the suction lance and wets it, and prior to being fed into the pipetting container can collect at the open end of the suction lance to form a liquid droplet of a defined size.

In a preferred embodiment the second end of the insertion lance comprises an insertion funnel. This ensures simplified feed-in of the liquid from the insertion nozzle to the liquids duct.

In a further preferred embodiment the suction lance and the insertion lance can be moved along a common axial direction. In this way the lances can be lowered in order to feed in or remove by suction a liquid into the pipetting container.

The suction lance and the insertion lance can, in particular, be movable independently from each other along the axial direction. This makes it possible, for example, for the suction lance to be moved from the insertion lance and for the purpose of drawing off a liquid to be lowered down to the bottom of the pipetting container.

In a pipetting device according to the invention the second open end of the insertion lance is preferably connected to a first reservoir by way of a first connecting pipe, and furthermore the second open end of the suction lance is connected to a second reservoir by way of a second connecting pipe.

In this way the liquid to be fed into the pipetting container can be removed from the first reservoir by way of the first connecting pipe, whereas the liquid removed by suction from the pipetting container is fed to the second reservoir by way of the second connecting pipe.

The first connecting pipe can comprise a feed valve that is arranged between the insertion lance and the first reservoir and that is situated in close proximity to the second open end of the insertion lance, wherein the distance between the feed valve and the second open end is preferably smaller than ten times the internal diameter of the first connecting pipe, or no more than 2 cm. By means of a feed valve that is situated in close proximity to the second open end of the insertion lance, and thus to the liquids duct, the point in time of the injection and the injection dose can be determined with great accuracy.

In a preferred embodiment the second connecting pipe comprises a suction removal valve between the second open end of the suction lance and the second reservoir.

The feed valve and/or the suction removal valve are preferably electronically controllable 3/2 valves.

In a further preferred embodiment the first reservoir is connected to a first pressure source by way of a first pressure pipe. This makes it possible to feed a liquid to the liquids duct by way of the first connecting pipe in that the first reservoir is pressurised by means of the first pressure source by way of the first pressure pipe, wherein metering is controlled with the use of the feed valve. In this way a precisely metered quantity of liquid can be injected into the pipetting container by means of a pressure surge.

In a preferred embodiment the pressure source is a nitrogen pressure source.

In an advantageous embodiment the first pressure pipe comprises a pressure reducer and/or a filter between the first reservoir and the first pressure source. The pressure reducer makes it possible to set the working pressure range, while the filter protects the reservoir and the liquid stored therein from contamination.

In a preferred embodiment the second reservoir is connected to a negative-pressure source by means of a second pressure pipe. In this way the second reservoir and the second connecting pipe, which is connected to said second reservoir, can be subjected to negative pressure so that by means of controlling the suction removal valve a liquid can be drawn off from the pipetting container through the suction lance into the second connecting pipe and from there into the second reservoir.

In a further preferred embodiment the negative-pressure source comprises a vacuum pump. In an alternative embodiment the negative-pressure source comprises a venturi nozzle that is connected to the first pressure source, which venturi nozzle converts overpressure of the first pressure source to negative pressure. In this embodiment, liquids can be both injected into the pipetting container and removed by suction from the pipetting container with the use of a single pressure source.

In an advantageous embodiment the insertion lance is connected to a first drive unit, and the suction lance is connected to a second drive unit. The first and/or the second drive unit are preferably pneumatic drive units.

As a result of the drive of the insertion lance and of the suction lance being implemented pneumatically, the design space required by the drive unit can be significantly reduced. Therefore the coaxial needle with the two drive units can advantageously be taken together to form a movable pipetting unit whose design height along an axial direction of the coaxial needle does not exceed 4 cm. The low design height in axial direction makes it possible, in particular, to move such a pipetting unit into the space between a stage or pipetting container and an illumination device of a microscope without this impeding operation of the microscope or requiring any design modification of the microscope.

In a preferred embodiment the first drive unit comprises a first pressure piston as well as a first connecting element and a first fastening element or fastening means, wherein the first fastening means can be connected to the insertion lance, and by way of the first connecting element can be connected to the first pressure piston. The second drive unit comprises a second pressure piston as well as a second connecting element and a second fastening element, wherein the second fastening element or fastening means is connected to the suction lance, and by way of the second connecting element can be connected to the second pressure piston.

In a preferred embodiment the first fastening element furthermore comprises the insertion nozzle for the uptake of a liquid from the first reservoir, and the second fastening element comprises the suction removal nozzle for delivery of the taken-up liquid to the second reservoir by way of the second connecting pipe. In this way the design space required by the pipetting unit can be further reduced.

In a further preferred embodiment the first fastening element is connected to the second fastening element by way of a spring, and can be connected by way of a driving pin. In this manner the insertion lance and the suction lance can together be lowered into the pipetting container with the use of only a single drive unit, as will be explained below with reference to an exemplary embodiment.

In an advantageous embodiment the first drive unit is connected to a second pressure source by way of a third pressure pipe, and the second drive unit is connected to said second pressure source by way of a fourth pressure pipe. In a preferred embodiment the second pressure source is identical to the first pressure source. In such an arrangement both the lances of the coaxial needle, and the liquids, can be driven with the use of a single pressure source. In this way a particularly compact and efficient pipetting device is implemented.

In a preferred embodiment the third pressure pipe comprises a first quick-exhaust throttle valve as well as a first drive valve, wherein the first quick-exhaust throttle valve is arranged between the first pressure piston and the first drive valve.

The quick-exhaust throttle valve results in a slower pressure build-up at the first drive unit, thus making it possible to reduce the movement speed during lowering of the insertion lance along its axial direction.

Correspondingly the fourth pressure pipe can comprise a second quick-exhaust throttle valve as well as a second drive valve, wherein the second quick-exhaust throttle valve is arranged between the second pressure piston and the second drive valve.

In a preferred embodiment the first drive valve and the second drive valve are electronically controllable 3/2 valves.

In a preferred embodiment the pipetting device according to the invention comprises a pipetting unit that can be moved in a direction perpendicular to an axial direction of the coaxial needle, which pipetting unit comprises the coaxial needle together with the first drive unit and the second drive unit, wherein the design height of the pipetting unit along an axial direction does not exceed 4 cm.

The invention also relates to a pipetting device with a pipette for feeding a liquid into a pipetting container and with a drive unit for moving the pipette, wherein the drive unit is a pneumatic drive unit and is connected to a first pressure source by way of a third pressure pipe.

As explained above, the pneumatic drive makes it possible to implement a particularly compact pipetting device, in particular a pipetting unit of a particularly low design height along an axial direction of the pipette, which pipetting device comprises the pipette and the drive unit.

In an advantageous embodiment the pipetting device additionally comprises a first connecting pipe that connects the pipette to a first reservoir, wherein the first reservoir is connected to the first pressure source by way of a first pressure pipe. In this way both the drive unit for moving the pipette and the injection device for feeding-in the liquid can be operated by way of a shared pressure source so that again a particularly compact and efficient pipetting device results.

The pipette of the pipetting device according to the invention can furthermore be designed for drawing off a liquid from a pipetting container, and can be connected to a second reservoir by way of a second connecting pipe, wherein the second reservoir is connected to a negative-pressure source by way of a second pressure pipe.

The negative-pressure source in turn can comprise a venturi nozzle that is connected to the first pressure source, as a result of which the advantages described above arise.

The invention also relates to a microscope with a pipetting device with the characteristics described above. In particular, the microscope can be an inverse microscope.

Lastly, the invention relates to a method for pipetting in which method a coaxial needle with a hollow suction lance and with a hollow insertion lance that encloses the suction lance at least in part is positioned above a pipetting container, the suction lance and the insertion lance are together moved into the pipetting container, a liquid is fed from a first reservoir for liquid to a liquids duct that is arranged between an exterior wall of the suction lance and an interior wall of the insertion lance, and the liquid is fed from the liquids duct into the pipetting container.

In a preferred embodiment a first end of the suction lance is positioned in the interior of the insertion lance so that the distance between a first open end of the suction lance, which end is opposite the pipetting container, and a first open end of the insertion lance, which open end is opposite the pipetting container, during feed-in of the liquid into the pipetting container is at least 1 mm. As explained above, in this manner the droplet formation in the liquids duct is enhanced, and injection without any splashing becomes possible.

In a further preferred embodiment the liquid is fed droplet by droplet into the pipetting container, wherein the volume of the droplets is set by means of selecting the distance between a first open end of the suction lance, which end is opposite the pipetting container, and a first open end of the insertion lance, which end is opposite the pipetting container. During feed-in of the liquid into the pipetting container the distance is preferably at least 1 mm.

In a preferred embodiment the step of moving the suction lance and the insertion lance involves penetration of a cover of the pipetting container.

In a further preferred embodiment the liquid is injected into the pipetting container by means of a pressure surge. As explained above, in this way the injected quantity of liquid can be metered out effectively and the point in time of injection can be determined with precision.

Furthermore, in a preferred embodiment the method according to the invention additionally comprises the step of connecting a second open end of the suction lance to a first negative-pressure source, as well as the removal by suction of excess liquid from the liquids duct through the interior of the suction lance into a second reservoir for liquid.

Removing by suction any excess liquid from the liquids duct reduces the danger of unintended feed-in of excessive quantities of liquid into the pipetting container. Furthermore, with the use of the method according to the invention the liquids duct can be cleaned in a simple manner by means of removal by suction. This is advantageous in particular in those instances where during a test series or between subsequent test series the liquid to be fed in is to be changed, and contamination of a subsequently used liquid with remainders of the previously used liquid must be avoided.

In a further preferred embodiment the method according to the invention additionally comprises the step of moving the suction lance along a shared axial direction of the suction lance and the insertion lance until a first open end of the suction lance is immersed in a volume of liquid within the pipetting container, and further comprises connecting a second open end of the suction lance to a second negative-pressure source and removing by suction a liquid from the pipetting container through the interior of the suction lance into a third reservoir for liquid.

Because the suction lance can be lowered along a shared axial direction independently of the insertion lance, a liquid can be effectively and completely removed by suction from the interior of the pipetting container even if the liquid level is low.

In a preferred embodiment the second negative-pressure source and the first negative-pressure source are identical, and/or furthermore the third reservoir for liquid and the second reservoir for liquid are identical.

Due to the compact design and the low design height the coaxial needle according to the invention or the pipetting device according to the invention can be used together with many widely-used types of microscopes without mutual interference, and they additionally make it possible to implement fast and controlled automated injection of liquids into a pipetting container, as well as the removal by suction of liquids from a pipetting container.

BRIEF DESCRIPTION OF THE DRAWING FIGURES

Figure 4B:
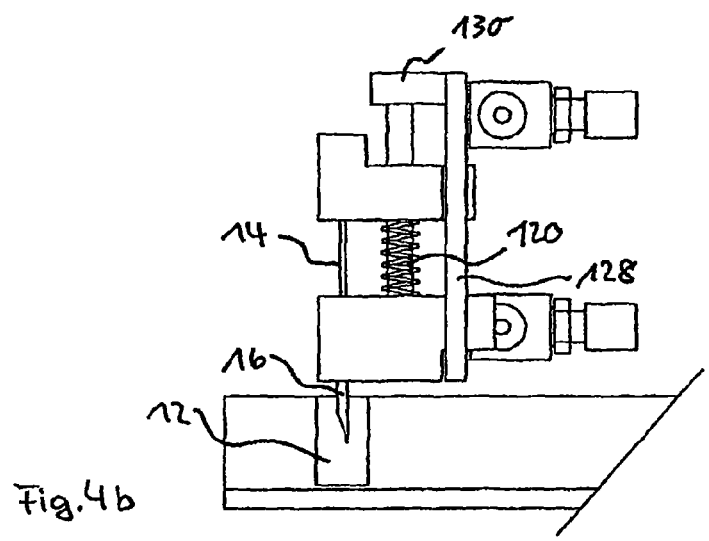
Figure 4C:
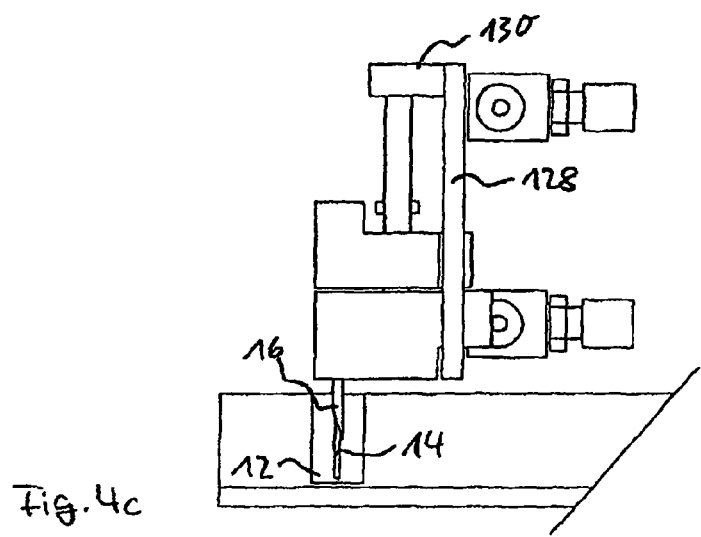
Figure 5:
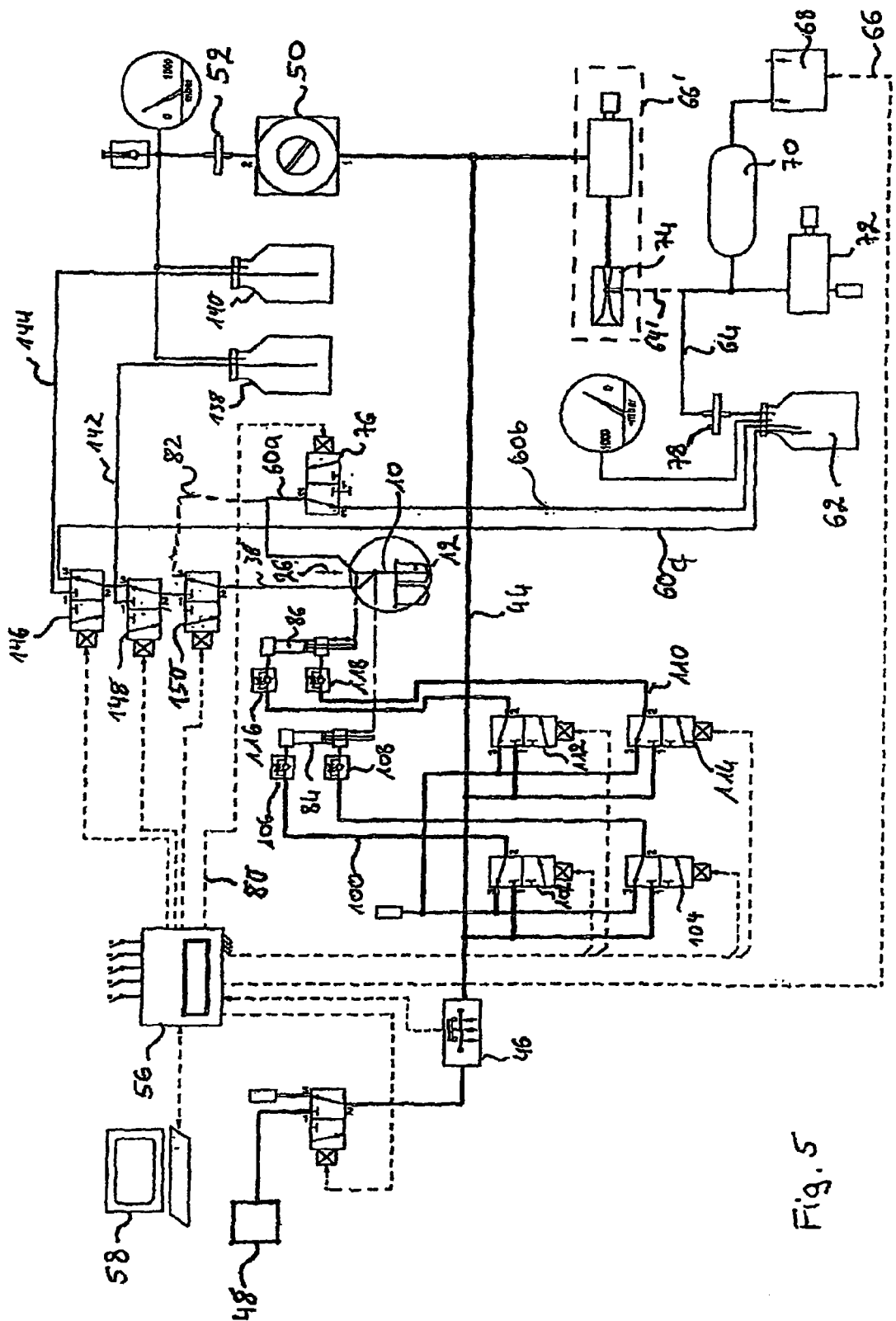

The numerous advantages of the coaxial needle according to the invention as well as of the pipetting device according to the invention and of the pipetting method according to the invention are best understood with reference to the detailed description of the enclosed drawings which show the following:

FIG. 1a a diagrammatic overview drawing of a preferred embodiment of the pipetting device according to the invention;

FIG. 1b an enlarged view of the quick-exhaust throttle valves used in the pipetting device of FIG. 1a;

FIGS. 2a-2d a preferred embodiment of a coaxial needle according to the invention in various operating positions;

FIGS. 3a-3c a diagrammatic lateral view of the drive device for operating the coaxial needle according to the invention in various operating positions;

FIGS. 4a-4c a diagrammatic front view of the drive device in the various operating positions of FIGS. 3a-3c; and FIG. 5 an improvement of the pipetting device according to the invention with several reservoirs for liquid.

DETAILED DESCRIPTION OF THE INVENTION

FIG. 1a shows a diagrammatic overview of a pipetting device according to the invention with the components essential to its operation. In the drawing of FIG. 1a the pressure pipes comprising supply pressure are shown in double solid lines, the pressure pipes comprising reduced overpressure or negative pressure are shown in single solid lines, while the control signal lines are shown in dashed lines. The centre of the pipetting device shows a coaxial needle 10 according to the invention, which is partly immersed in a pipetting container 12. The pipetting container 12 can, for example, be a cylindrical probe chamber of a well plate or of a Petri dish, which probe chamber comprises a cell probe and if applicable a liquid that has been fed to the probe, and has been inserted into the optical path of an inverse optical microscope (not shown in FIG. 1a).

Below, the design and function of the coaxial needle 10 are described in detail with reference to FIGS. 2a-2d.

FIG. 2a shows the coaxial needle 10 in a parked position above the pipetting container 12 sealed with a cover foil 30. As shown in the diagram, the coaxial needle 10 comprises a suction lance 14 as well as an insertion lance 16. Both lances are designed in the form of a metallic hollow cylinder, wherein the insertion lance 16 is shorter than the suction lance 14 and comprises an internal diameter that exceeds the external diameter of the suction lance.

In the embodiment described, both the suction lance 14 and the insertion lance 16 are in the shape of hollow regular cylinders. However, depending on the field of use of the needle it is possible to use hollow bodies of different shapes. In the context of the present invention the term "suction lance" refers to any hollow body that is suitable for drawing off a liquid. Correspondingly the term "insertion lance" refers to any hollow body that in cooperation with the suction lance is suitable for feeding a liquid into a pipetting container 12. The insertion lance can, in particular, be designed to pierce a cover foil 30.

As shown in FIG. 2a, the suction lance 14 comprises a first open end 18 that is opposite the pipetting container 12, and a second open end 20 that is opposite the first open end 18 along an axial direction 26. Correspondingly the insertion lance 16 comprises a first open end 22 that is opposite the pipetting container 12, and a second open end 24 that is opposite the first open end 22. The first open end 18 of the suction lance 14 is inserted into the insertion lance 16 and is slidable therein, wherein the insertion lance 16 encloses the suction lance 14 partly coaxially, but the suction lance 14 due to its longer length always at least on one side projects from the insertion lance 16. Since the internal diameter of the insertion lance 16 is larger than the external diameter of the suction lance 14, at the position where the insertion lance 16 coaxially encloses the suction lance 14 a liquids duct 28 is formed between an outer wall of the suction lance 14 and an inner wall of the insertion lance 16.

In the arrangement shown in FIG. 2a, the first open end 22 of the insertion lance 16 is designed in the form of a tip bevelled relative to the axial direction 26. This tip is used to penetrate the cover foil 30 when the coaxial needle 10 is lowered into the pipetting container 12.

At its second open end 24 the insertion lance 16 comprises an insertion funnel 32 by way of which from an insertion nozzle 34 connected to the insertion lance 16 a liquid can be inserted into the liquids duct 28. In contrast to this, at its second open end 20 the suction lance 14 is connected to a suction removal nozzle 36, by way of which a liquid can be removed by suction from the interior of the suction lance 14.

As shown in FIG. 1, by way of a first connecting pipe 38 and a feed valve 40, the insertion nozzle 34 is connected to a first reservoir 42 in which a liquid that is to be injected into the pipetting container 12 is stored. The first connecting pipe 38 can be a flexible plastic hose. The first reservoir 42 is connected to a pressure source 48 by way of a first pressure pipe 44 and a pressure switch 46. The pressure source 48 can be a pressure source that is operated with the use of nitrogen as a working gas, which pressure source provides a working pressure of approximately 5 bar. By way of a pressure reducer 50, which is arranged between the pressure source 48 and the first reservoir 42, this working pressure is converted to a reduced pressure of approximately 0.2 to 0.3 bar. A filter 52 arranged downstream of the pressure reducer 50 protects the first reservoir 42 and the liquid stored therein from contamination.

The feed valve 40 is a so-called 3/2-valve that is magnetically operated and that provides three connections with two switching states. The illustration in FIG. 1 shows both possible switching states of the feed valve 40 side by side, namely on the left-hand side the feed valve 40 open for the infeed of a liquid from the first reservoir 42 to the coaxial needle 10, in which feed valve 40 the connections 1 and 2 are connected in the direction of passage, and on the right-hand side the blocked valve, in which the connections 2 and 3 are connected and the infeed of liquid from the first reservoir 42 to the pipette 10 is blocked.

By way of a first control line 54, which connects the feed valve 40 to a control unit 56, it is possible to electronically change, in a preselected timing pattern, between the two switching states of the feed valve 40, and in this way to control the infeed of liquid to the pipette. Typical switching times of such a valve range between 10 ms and 50 ms. An input/output unit 58 that is connected to the control unit 56 is used to select and enter suitable timing sequences and to control and monitor the pipetting device.

The first feed valve 40 is arranged so as to be in close proximity to the coaxial needle 10, wherein the distance between the second open end 24 of the insertion lance 16 and the feed valve 40 is preferably smaller than ten times the diameter of the first connecting pipe 38, or no more than 2 cm. In this way the quantity and the point in time of the infeed of liquid can be determined particularly accurately.

The second open end 20 of the suction lance 14 is connected to a second reservoir 62 by way of the suction removal nozzle 36 and a second connecting pipe 60a, 60b, which reservoir 62 in turn is connected to a negative-pressure source 66 by way of a second pressure pipe 64. The second connecting pipe 60a, 60b can also comprise a flexible plastic hose.

In a first embodiment the negative-pressure source 66 not only comprises a conventional vacuum pump 68, for example a sliding-vane rotary pump, but also a buffer volume 70 as well as a needle-valve bypass 72.

The drawing in FIG. 1 also shows an alternative embodiment with a negative-pressure source 66'. In this alternative embodiment the second reservoir 62 is coupled to the low-pressure connection of a venturi nozzle 74 by way of a second pressure pipe 64'. The venturi nozzle 74 in turn is connected to the first pressure pipe 44 and thus to the pressure source 48 and in this way transforms overpressure in the first pressure pipe 44, which overpressure is provided by the pressure source 48, to negative pressure in the second pressure pipe 64'.

By way of a suction removal valve 76 in the second connecting pipe 60a, 60b, the suction removal nozzle 36 and the second open end 20, connected to it, of the suction lance 14 can be controlled with negative pressure (in the embodiment shown −50 mbar to −100 mbar) so that a liquid from the pipetting container 12 can be removed by suction, through the suction lance 14, the second connecting pipe 60a, 60b and the suction removal valve 76, into the second reservoir 62. A filter 78 in the second pressure pipe 64 or 64' prevents liquids or their outgassing products from being removed by suction from the second reservoir 62 into the negative-pressure source 66 or 66'.

As is the case in the feed valve 40 described above, the suction removal valve 76 can be an electronically controlled 3/2 valve, which is connected to the control unit 56 by way of a second control line 80. The first switching state, shown on the left-hand side in the illustration of FIG. 1, in which switching state the connections 2 and 3 are connected, is the active switching state of the suction removal valve in which the coaxial needle 10 is connected to the negative-pressure source 66 or 66' by way of the second connecting pipe 60a, 60b. The inactive or closed switching state, in which the connections 1 and 2 of the suction valve 76 are interconnected, is shown on the right-hand side adjacent.

In the embodiment shown in FIG. 1, the feed valve 40 and the suction removal valve 76 can be coupled by way of an intermediate connection 82 which connects connection 3 of the feed valve with connection 2 of the suction valve. This intermediate connection 82 makes it possible to empty and evacuate the first connecting pipe 38 and the insertion nozzle 34 and thus the liquids duct 28 by means of the negative-pressure source 66 or 66' when all the liquid is to be discharged from the pipetting device, for example for cleaning work or maintenance work.

The diagrammatic overview drawing of FIG. 1 also shows the pneumatic drive unit for operating the coaxial needle 10. The pipetting device shown provides for two separate drive units 84 and 86 for the insertion lance 16 and the suction lance 14 so that the insertion lance 16 and the suction lance 14 can be moved independently of each other along their common axial direction 26.

Below, the drive units 84 and 86 are described in detail with reference to FIG. 3a.

The first drive unit 84 comprises a first pressure piston 88 as well as a first connecting element 90 and a first fastening element 92. The first fastening element 92 is directly connected to the insertion lance 16 and also comprises the insertion nozzle 34 (not shown in the illustration of FIG. 3a). The first fastening element 92 is connected to the first pressure piston 88 by way of the first connecting element 90. In this manner, by way of the first connecting element 90, the movement of the first pressure piston 88 is translated into a movement of the insertion lance 16 along the axial direction 26 (compare FIG. 2).

The second drive unit 86 for moving the suction lance 14 is designed in a similar manner; it comprises a second pressure piston 94, a second connecting element 96 that is connected to the second pressure piston 94 and the first connecting element 90, as well as a second fastening element 98. The second fastening element 98 is directly connected to the suction lance 14 and also comprises the suction removal nozzle 36 (not shown in the illustration of FIG. 3a). When the second pressure piston 94 is activated, the second connecting element 96 acts on the second fastening element 98 and in this manner makes it possible for the suction lance 14 to move along the axial direction 26.

The drive unit according to the invention as well as the design, according to the invention, of the coaxial needle 10 make it possible to implement a movable pipetting unit 126 which comprises both the coaxial needle 10 and the first drive device 84 and the second drive unit 86, with the design height along the axial direction 26 of said pipetting unit 126 being low enough for the pipetting unit 126 to be able to be inserted between a pipetting container 12 and an illumination unit, arranged above the pipetting container 12, of an inverse optical microscope of conventional design, without microscopy operation and pipetting operation interfering with each other. In particular, it is possible to achieve pipetting units 126 with design heights along the axial direction 26 of less than 4 cm.

As shown in the overview drawing of FIG. 1, the first pressure piston 88 of the first drive unit 84 is connected to the first pressure pipe 44 and thus to the pressure source 48 by way of a third pressure pipe 100. By way of two drive valves 102 and 104 the third pressure pipe 100 is coupled to the first pressure pipe 44 so that depending on the switching state the first pressure piston 88 can be subjected to pressure on both ends, wherein pressurisation from one end is translated into a downward movement of the insertion lance 16 by way of the first connecting element 90, whereas pressurisation from the opposite end is translated into an upward movement of the insertion lance 16 along the axial direction.

The drive valves 102 and 104 again are electronically controllable 3/2 valves whose switching states in the illustration of FIG. 1 among each other are shown, with said valves again being connected to the control unit 56 by way of the control lines that are shown in dashed lines.

In both branches of the third pressure pipe 100, quick-exhaust throttle valves 106 and 108 are arranged upstream of the first pressure piston 88, which quick-exhaust throttle valves 106 and 108 delay pressure build-up at the first pressure piston 88 and in this manner make it possible to set the movement speed of the insertion lance 16.

The second pressure piston 94 is correspondingly connected to the first pressure pipe 44, which in turn comprises two electronically controllable 3/2 valves 112 and 114 that are connected to the control unit 56. In this arrangement the drive of the second pressure piston 94 takes place analogously to the above-described drive of the first pressure piston 88, wherein again quick-exhaust throttle valves 116 and 118 are provided in both branches of the fourth pressure pipe 110.

The action and function of the quick-exhaust throttle valves 106, 108, 116 and 118 that are used is diagrammatically illustrated in the enlarged section of FIG. 1b. Such a valve comprises a nonreturn valve 132 that in the case of a flow from the end of the throttle valve, which end faces the pressure source 48 and in FIG. 1b is designated A, to the end of the valve that faces the lifting cylinder of the pipetting unit and that in FIG. 1b is designated B blocks said flow while enabling a flow in the opposite direction. Furthermore, the throttle valve comprises a bypass 134 which bypasses the nonreturn valve 132 and that comprises a reducing valve 136 that can be regulated.

The pressure build-up on the lifting cylinder takes place more slowly because the pressure medium can flow in the flow direction A→B only through the bypass 134 whose capacity is limited by the reducing valve 136. In contrast to this, the pressure reduction on the lifting cylinder can take place suddenly because in the flow direction B→A both the nonreturn valve 132 and the reducing valve 136 are open to the pressure medium. With suitable selection of the flow-through capacity at the reduction valve 136, the pressure build-up and thus the movement speed of the insertion lance 16 or the suction lance 14 can be set accordingly.

For pipetting, the coaxial needle 10 as well as the pipetting unit 126 comprising the first drive unit 84 and the second drive unit 86 are positioned above a selected pipetting container 12. Such positioning can take place on the one hand in that, by means of a movable positioning device on the stage of a microscope, the pipetting container 12 is moved underneath the coaxial needle 10. As already explained, as an alternative, the pipetting device according to the invention also makes it possible for the pipetting unit 126 to be designed so as to be movable. To this effect the pipetting unit 126 can then be connected to a drive device (not shown in the illustration of FIG. 1), which drive device makes it possible for the pipetting unit 126 to move along the plane of the stage and if need be also perpendicularly to said plane. For example, for filling and emptying a selected chamber of the pipetting container, a movable pipetting unit 126 can be swung into the optical path of the microscope and during the subsequent microscopy process can be swung out of the optical path. This ensures trouble-free microscopy operation even for observation in transmission.

Because of the low design height of the pipetting unit 126 along the axial direction 26, the pipetting device 126 according to the invention can be used together with a multitude of commonly used microscope models and designs without pipetting operation and microscopy operation causing mutual interference. In particular, the coaxial needle 10 can be inserted into the optical path between the stage with the pipetting container 12 and an illumination device of the microscope, which illumination device is arranged above the stage. The pipetting device according to the invention can thus be used irrespective of the microscope that is used for observation providing for illumination from above the object, from below the object, or, as is the case in the microscope described in patent specification U.S. Pat. No. 7,092,151 B2, selectively from above or below the stage. This is one of the special advantages of the coaxial needle according to the invention and of the pipetting device according to the invention.

Furthermore, due to its compact design the pipetting device according to the invention is particularly suitable for use in climatic chambers.

The method for pipetting is explained below with reference to the embodiments shown in FIGS. 2, 3 and 4. In this arrangement FIGS. 2a, 3a and 4a show the coaxial needle 10 in a parked position; FIGS. 2b, 2c, 3b and 4b show the coaxial needle 10 in an injection position, and FIGS. 2d, 3c and 4c show the coaxial needle 10 in a suction removal position.

In the parked position shown in FIGS. 2a, 3a and 4a the coaxial needle 10 is situated above a pipetting container 12 that is sealed by means of a cover foil 30, which pipetting container 12 contains the cell probe to be investigated.

In order to insert the coaxial needle 10 into the pipetting container 12, pressure is applied to the first pressure piston 88 by way of the third pressure pipe 100 so that the insertion lance that is connected to the first pressure piston 88 by way of the first fastening element 92 and the first connecting element 90 moves downwards along the axial direction 26. At the same time the second connecting element 96, which is coupled to the first connecting element 90, is made to establish contact with the second fastening element 98, as illustrated in the diagram of FIG. 3b. As shown in the diagram of FIG. 3a, the first fastening element 92 of the insertion lance 16 is coupled to the second fastening element 98 of the suction lance 14 by way of a spring 120 that is released in the parked position and by way of a driving pin 130. As shown in FIG. 4a, the first fastening element 92 and the second fastening element 98 are additionally guided together in a guide rail 128 that extends in axial direction 26. When the first fastening element 92 and with it the insertion lance 16 moves along the guide rail 128 into the pipetting container 12, a pin 130, which is connected to the first fastening element 92 and whose widened cover surface engages the second fastening element 98, pulls the suction lance 14, which is firmly connected to the second fastening element 98, along. While maintaining their relative positions, both the insertion lance 16 and the suction lance 14 move into the pipetting container 12, and the insertion tip of the insertion lance 16 penetrates the cover foil 30. The coaxial needle is then in the injection position shown in FIGS. 2b and 2c, as well as 3b and 4b.

As a result of activation of the feed valve 40, the liquid to be fed-in is channeled under pressure from the first reservoir 42, by way of the first connecting pipe 38, the insertion nozzle 34 and the insertion funnel 32, into the liquids duct 28 between the suction lance 14 and the insertion lance 16. As shown in FIG. 2b, the liquid flows around the suction lance 14 and at its first open end 18 collects to form a droplet. In the embodiment shown the distance between the first open end 18 of the suction lance 14, which open end is opposite the pipetting container 12, and a first open end 22 of the insertion lance, which end 22 is opposite the pipetting container 12, during feed-in of the liquid into the pipetting container 12 is approximately 1 mm. By means of suitable selection of this distance, which in the embodiment shown can be adjusted by displacement of the pin 130, the droplet size and thus the volume of injected liquid can be set correspondingly. By means of a pressure surge of the feed valve 40 the droplet is detached from the coaxial needle 10 and falls into the pipetting container 12. Apart from droplet injection, injection of the liquid in constant flow is also possible in that the feed valve 40 is kept open for an extended period of time by way of the control unit 56.

By connecting the second open end 20 of the suction lance 14 to the negative-pressure source by way of the second connecting pipe 60a, 60b and the suction removal valve 76, in a subsequent step, illustrated in FIG. 2c, if required after detachment of the droplet, any remaining liquid still in the liquids duct 28 can be removed by suction into the second reservoir 62 by way of the interior of the suction lance 14.

Subsequently the coaxial needle 10 can be removed from the pipetting container 12 in that as a result of activation of the first drive unit 84 the insertion lance 16 is moved along the guide rail 128 back into the home position. Since the second fastening element 98 of the suction lance 14 is connected to the first fastening element 92 of the insertion lance 16 by way of the spring 120, in this process at the same time the suction lance 14 is moved back from the pipetting container 12 while said suction lance 14 maintains its relative position to the insertion lance 16. The coaxial needle 10 can then be positioned above a further pipetting container in order to repeat the injection process.

However, the pipetting device according to the invention can also be used for removing by suction a liquid from a pipetting container 12. To this effect, according to the method described above, the insertion lance 16 and the suction lance 14 are first jointly inserted into a selected pipetting container 12. Following the feed-in of such a liquid, or as an alternative also without such a preceding injection step, to this effect the coaxial needle 10 is moved to the suction removal position shown in FIGS. 2d, 3c and 4c. Starting from the injection position shown in FIGS. 2b, 2c, 3b and 4b, the second pressure piston 94 is activated by way of the fourth pressure pipe 110 so that the second connecting element 96, which is connected to the second pressure piston 94, engages the second fastening element 98, and the suction lance 14 under tension of the spring 120 is lowered in axial direction 26 along the guide rail 128 until the first open end 18 of the suction lance 14 is immersed into the volume of liquid 124 that has collected in the pipetting container 12. In this process the position of the insertion lance 16 remains unchanged. By connecting the second open end 20 of the suction lance 14, by way of the suction removal nozzle 36 and the second connecting pipe 60a, 60b, to the negative-pressure source 66 or 66', the volume of liquid 124 collected in the pipetting container 12 can subsequently partly or completely be removed by suction through the interior of the suction lance 14 into the second reservoir 62. After completion of the suction process, the spring 120 is released as a result of the return movement of the drive unit 86 or of the connecting element 96 so that the fastening element 98 is pushed upwards as a result of the spring force, and the suction lance 14 that is connected to the fastening element 98 bounces back along the axial direction 26 into its home position shown in FIGS. 2c, 3b and 4b. The method can now be continued as described above.

According to the method described above, with the pipetting device according to the invention liquids can quickly, reliably and in a precisely metered manner be fed into a sealed pipetting container or removed from a sealed pipetting container. However, in many test series sequential feed-in or removal of different liquids or of a liquid in different concentrations is desired. It is often necessary to prevent mutual contact among liquids so as to prevent any contamination or undesirable reaction.

To this purpose, the method according to the invention and the device according to the invention can be designed to comprise several separate liquids circulation systems, each comprising a coaxial needle while for the remainder corresponding to the embodiment described above. In order to inject one of the liquids into a selected pipetting container, or in order to remove by suction one of the liquids from a selected pipetting container the corresponding coaxial needle can then be selected in the revolver system.

As an alternative, instead of using several coaxial needles, a single coaxial needle can also be used, which is designed to be connected to different liquids circulation systems and which furthermore can be connected to a separate cleaning circulation system. Between the connection to different liquids circulation systems in this way cleaning of the coaxial needle can be carried out in order to effectively prevent any contamination. Cleaning can take place either by rinsing the pipe system with a separate rinsing liquid or by removal by suction of the remaining pipetting liquids from the liquids circulation system.

FIG. 5 shows a diagrammatic overview of a corresponding improvement of the pipetting device according to the invention. The pipetting device shown in FIG. 5 is in essential parts identical to the pipetting device shown in FIG. 1a, with corresponding components having the same reference characters. However, instead of comprising the first reservoir 42, the pipetting device shown in FIG. 5 comprises two reservoirs: one reservoir 138 for a first pipetting liquid, and one reservoir 140 for a second pipetting liquid. Furthermore, the improvement according to the invention, instead of comprising one feed valve 40, comprises three feed valves: a first feed valve 146, a second feed valve 148 and a third feed valve 150. The first, second and third feed valves in the embodiment shown are 3/2 valves that are electronically controllable by way of the control unit 56, as explained above with reference to the illustration of FIG. 1a.

By way of the connecting pipe 142 or the connecting pipe 144 it is possible, selectively under pressure, to feed to the insertion lance 16 a defined quantity of the first pipetting liquid from the reservoir 138 or to the second pipetting liquid from the reservoir 140. To this effect the connecting pipe 142 for the first pipetting fluid is connected to the input port 1 of the second feed valve 148. The output port 2 of the second feed valve 148 in turn is in contact with the input port 1 of the third feed valve 150, whose output port leads to the insertion lance 16 by way of the first connecting pipe 38. By activation of the second feed valve 148 and of the third feed valve 150 liquid is therefore fed from the reservoir 138 for the first pipetting liquid to the pipette. The first feed valve 146, which is connected to the reservoir 140 for the second pipetting liquid by way of the connecting pipe 144, is decoupled at this point in time.

If instead of feeding the first pipetting liquid the second pipetting liquid is to be fed to the pipette, then instead of the second feed valve 148 and the third feed valve 150, the first feed valve 146 and the third feed valve 150 are activated. In this manner the second pipetting liquid can be fed under pressure to the insertion lance 16 by way of the connecting pipe 144 and the first feed valve 146, the inactive second feed valve 148 and the third feed valve 150, while the first pipetting liquid, which is connected to the inactive input port 1 of the second feed valve 148 by way of the connecting pipe 142, is decoupled. The input port 3 of the first feed valve 146 is connected to the second reservoir 62 by way of a connecting pipe 60c, which reservoir 62 takes up any residues removed by suction from the pipe system of the pipetting device.

With the improvement described, selectively either the first or the second pipetting liquid can be injected. In order to prevent mutual contamination of the pipetting liquids, the pipe system can be cleaned by suction removal between injection of the first pipetting liquid and injection of the second pipetting liquid, with cleaning taking place, for example, in that the first connecting pipe 38 is connected to the suction removal valve 76 by way of connection 3 of the third feed valve 150, as correspondingly illustrated in FIG. 1a by the intermediate connection 82, or for example by activation of the valve 150 and of the connection 2-3 by way of the inactive valves 148 and 146 and the connecting pipe 60c into the container 62.

In the same manner the pipetting device according to the invention can be expanded, by the addition of further reservoirs and feed valves, to operate with more than two pipetting liquids.

The embodiments described above and the illustrating drawings only serve to explain the device according to the invention and the method according to the invention; they should in no way be misinterpreted as limitations. The scope of protection of the invention is based solely on the following claims.

LIST OF REFERENCE CHARACTERS

10 Coaxial needle
12 Pipetting container
14 Suction lance
16 Insertion lance
18 First open end of the suction lance 14
20 Second open end of the suction lance 14
22 First open end of the insertion lance 16
24 Second open end of the insertion lance 16
26 Axial direction
28 Liquids duct
30 Cover foil
32 Insertion funnel
34 Insertion nozzle
36 Purge nozzle
38 First connecting pipe
40 Feed valve
42 First reservoir
44 First pressure pipe
46 Pressure switch
48 Pressure source
50 Pressure reducer
52 Filter
54 First control line
56 Control unit
58 Input/output unit
60a, 60b, 60c Second connecting pipes
62 Second reservoir
64, 64' Second pressure pipe
66, 66' Negative-pressure source
68 Vacuum pump
70 Buffer volume
72 Needle-valve bypass
74 Venturi nozzle
76 Suction removal valve
78 Filter
80 Second control line
82 Intermediate connection
84 First drive unit
86 Second drive unit
88 First pressure piston
90 First connecting element
92 First fastening element
94 Second pressure piston
96 Second connecting element
98 Second fastening element
100 Third pressure pipe
102, 104 Drive valves for first drive unit 84
106, 108 Nonreturn reducing valves for first drive unit 84
110 Fourth pressure pipe
112, 114 Drive valves for second drive unit 86
116, 118 Nonreturn reducing valves for second drive unit 86
120 Spring
122 Excess liquid
124 Volume of liquid in the pipetting container 12
126 Pipetting unit
128 Guide rail
130 Driving pin
132 Nonreturn valve
134 Bypass
136 Reducing valve
138 Reservoir for first pipetting liquid
140 Reservoir for second pipetting liquid
142 Connecting pipe for first pipetting liquid
144 Connecting pipe for second pipetting liquid
146 First feed valve
148 Second feed valve
150 Third feed valve

The invention claimed is:

1. A pipetting device comprising a pipetting unit, the pipetting unit comprising:
a hollow suction conduit for drawing off a liquid from a pipetting container, and
a hollow insertion lance that encloses the suction conduit at least in part so that, between an exterior wall of the suction conduit and an interior wall of the insertion lance, a liquids duct for feeding a liquid into a pipetting container is formed, wherein the insertion lance comprises a first open end for the delivery of a liquid to a pipetting container, and a second open end for the uptake of the liquid, wherein the hollow suction conduit and the hollow insertion lance are configured to provide a coaxial needle,
the pipetting unit further comprising:
a first drive unit connected to the insertion lance; and
a second drive unit connected to the suction conduit;
wherein the pipetting unit is configured to be moved in a direction perpendicular to an axial direction of the coaxial needle.

2. The pipetting device according to claim 1, wherein the suction conduit comprises a first open end for the uptake of a liquid from a pipetting container, and a second open end, which is arranged axially opposite the first open end, for the delivery of the taken-up liquid to a suction removal passageway and wherein the second open end is axially opposite the first open end and is adapted for the uptake of a liquid from an insertion nozzle.

3. The pipetting device according to claim 2, wherein the second open end of the suction conduit is connected to a second reservoir by way of a second connecting pipe.

4. A microscope comprising a pipetting device according to claim 3.

5. The pipetting device according to claim 1, wherein a design height of the pipetting unit along the axial direction does not exceed 4 cm.

6. The pipetting device according to claim 1, wherein the first drive unit and/or the second drive unit are pneumatic drive units.

7. The pipetting device according to claim 6, wherein the first drive unit comprises a first pressure piston as well as a first connecting element and a first fastening element, and wherein the first fastening element is configured to be connected to the insertion lance and to the first pressure piston by way of the first connecting element, and wherein, furthermore, the second drive unit comprises a second pressure piston, a second connecting element and a second fastening element, and wherein the second fastening element is connected to the suction conduit and is configured to be connected to the second pressure piston by way of the second connecting element.

8. The pipetting device according to claim 7, wherein the first fastening element is connected to the second fastening element by way of a spring and is configured to be connected by way of a driving pin.

9. The pipetting device according to claim 1, wherein the suction conduit and the insertion lance are configured to be moved along a shared axial direction.

10. The pipetting device according to claim 9, wherein the suction conduit and the insertion lance are configured to be moved along the axial direction independently of each other.

11. A method for pipetting comprising the following steps:
providing a pipetting device comprising a pipetting unit, the pipetting unit comprising:
a hollow suction conduit for drawing off a liquid from a pipetting container,
a hollow insertion lance that encloses the suction conduit at least in part so that, between an exterior wall of the suction conduit and an interior wall of the insertion lance, a liquids duct for feeding a liquid into a pipetting container is formed, a first drive unit connected to the insertion lance; and a second drive unit connected to the suction conduit, wherein the insertion lance comprises a first open end for the deliver of a liquid to a pipetting container, and a second open end for the uptake of the liquid, and wherein the hollow suction conduit and the hollow insertion lance are configured to provide a coaxial needle;
moving said pipetting unit in a direction perpendicular to an axial direction of the coaxial needle;
positioning the coaxial needle above a pipetting container;
together moving the suction conduit and the insertion lance into the pipetting container; feeding a liquid from a first reservoir for liquid to the liquids duct; and
feeding the liquid from the liquids duct into the pipetting container.

12. The method according to claim 11 with the following steps in addition:
connecting a second open end of the suction conduit to a first negative-pressure source; and
removing by suction excess liquid from the liquids duct through the interior of the suction conduit into a second reservoir for liquid.

13. The method according to claim 12 with the following steps in addition:
moving the suction conduit along a common axial direction of the suction conduit and of the insertion lance until a first open end of the suction conduit is immersed in a volume of liquid within the pipetting container;
connecting a second open end of the suction conduit to a second negative-pressure source; and
removing by suction at least part of the volume of liquid from the pipetting container through the interior of the suction conduit into a third reservoir for liquid.

* * * * *